United States Patent
Osasawara et al.

(10) Patent No.: US 7,737,291 B2
(45) Date of Patent: Jun. 15, 2010

(54) COMPOSITION CONTAINING SILOXANE COMPOUND AND PHENOL COMPOUND

(75) Inventors: Kunio Osasawara, Sendai (JP); Kazuhisa Onozawa, Tokyo (JP); Hiroki Sato, Tokyo (JP); Takashi Higashino, Tokyo (JP)

(73) Assignee: Adeka Corporation, Tokyo (JP)

( * ) Notice: Subject to any disclaimer, the term of this patent is extended or adjusted under 35 U.S.C. 154(b) by 677 days.

(21) Appl. No.: 11/597,036

(22) PCT Filed: Dec. 21, 2005

(86) PCT No.: PCT/JP2005/023476
§ 371 (c)(1), (2), (4) Date: Nov. 17, 2006

(87) PCT Pub. No.: WO2006/077712
PCT Pub. Date: Jul. 27, 2006

(65) Prior Publication Data
US 2007/0232821 A1 Oct. 4, 2007

(30) Foreign Application Priority Data
Jan. 18, 2005 (JP) .............................. 2005-009798

(51) Int. Cl.
*C23C 16/42* (2006.01)
*C07F 7/21* (2006.01)
(52) U.S. Cl. ..................................................... 556/401
(58) Field of Classification Search .................. 556/401
See application file for complete search history.

(56) References Cited

U.S. PATENT DOCUMENTS
7,129,311 B2 * 10/2006 Teff et al. ....................... 528/31
2002/0091205 A1  7/2002 Brewer et al.
2003/0149213 A1  8/2003 Mayorga et al.

FOREIGN PATENT DOCUMENTS
JP  7-145179  6/1995
JP  2003-238578  8/2003
WO  WO 2004/027110  4/2004

OTHER PUBLICATIONS
International Preliminary Report and Written Opinion issued on Aug. 2, 2007.
Chinese Patent Office issued a Chinese Office Action dated Sep. 11, 2009, Application No. 2005800227245.

* cited by examiner

*Primary Examiner*—Daniel M Sullivan
*Assistant Examiner*—Yevegeny Valenrod
(74) *Attorney, Agent, or Firm*—Young & Thompson

(57) ABSTRACT

A composition containing 100 parts by mass of a siloxane compound having —HSiRO— (wherein R is a hydrogen atom, a hydrocarbon group having 1 to 8 carbon atoms, an alkoxy group having 1 to 8 carbon atoms or a phenoxy group) and 0.0001 to 1 part by mass of at least one phenol compound of general formula (1) or (2) as a stabilizer.

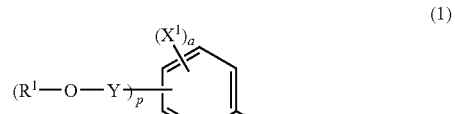

(1)

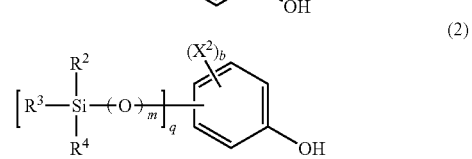

(2)

wherein a and b are each an integer of 0 to 4; m is 0 or 1; p and q are each 1 or 2; $R^1$, $R^2$, $R^3$, and $R^4$ are each an alkyl group having 1 to 4 carbon atoms; $X^1$ and $X^2$ each represent an alkyl group having 1 to 4 carbon atoms, an alkoxy group having 1 to 4 carbon atoms or a halogen atom; Y is an alkanediyl group having 1 to 4 carbon atoms; and a plurality of $R^1$s, $R^2$s, $R^3$s, $R^4$s, $X^1$s, $X^2$s or Ys, where present per molecule, may be the same or different.

10 Claims, No Drawings

COMPOSITION CONTAINING SILOXANE COMPOUND AND PHENOL COMPOUND

FIELD OF THE INVENTION

This invention relates to a composition of a siloxane compound having —HSiRO— (wherein R represents a hydrogen atom, a hydrocarbon group having 1 to 8 carbon atoms, an alkoxy group having 1 to 8 carbon atoms, or a phenoxy group) having incorporated therein a specific phenol compound as a stabilizer. The composition is useful as a material for thin film formation.

BACKGROUND OF THE INVENTION

A siloxane compound having —HSiRO— (wherein R represents a hydrogen atom, a hydrocarbon group having 1 to 8 carbon atoms, an alkoxy group having 1 to 8 carbon atoms, or a phenoxy group) is used as a precursor of a silicon oxide-based thin film. According to electric characteristic and optical characteristic, a silicon oxide-based thin film is applied as a low-dielectric-constant interlayer insulator for multilayer circuit structures for semiconductor devices or an optical component such as a microlens.

However, the above siloxane compound undergoes alteration due to polymerizing, which gives rise to a problem on use. For example, when applied to a wet coating technique including a sol gel process, a coating composition of the siloxane compound undergoes viscosity increase or gelation, failing to form a thin film stably. In application to thin film formation involving vaporization, it is difficult to vaporize a given amount of the precursor stably. Furthermore, a polymerization product can contaminate thin film formation equipment and a thin film formed and clog feed pipes.

To address the above problems, Patent document 1 discloses a combined use of a phenol compound, such as 2,6-di-t-butyl-4-methylphenol, with a siloxane compound, and Patent document 2 discloses a combined use of a phenol compound typified by 4-methoxyphenol with a siloxane compound. These conventionally proposed phenol compounds produce only insufficient stabilizing effects nevertheless.

Patent document 1: JP-A-2003-238578

Patent document 2: WO 2004/27110

BRIEF SUMMARY OF THE INVENTION

Accordingly, an object of the invention is to provide a siloxane compound-containing composition useful as a thin film forming material with excellent stability.

As a result of extensive investigations, the present inventors have found that a specific phenol compound produces a specific stabilizing effect on a siloxane compound and thus reached the present invention.

The present invention provides a composition containing 100 parts by mass of a siloxane compound having —HSiRO— (wherein R represents a hydrogen atom, a hydrocarbon group having 1 to 8 carbon atoms, an alkoxy group having 1 to 8 carbon atoms, or a phenoxy group) and 0.0001 to 1 part by mass of a phenol compound represented by general formula (1) or (2) below as a stabilizer.

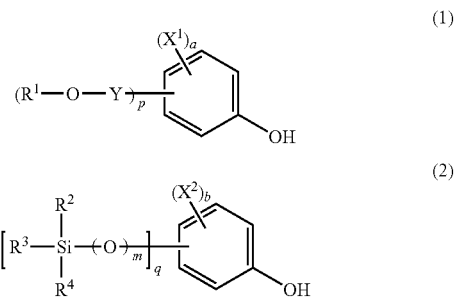

wherein a and b each represent an integer of 0 to 4; m represents 0 or 1; p and q each represent 1 or 2; $R^1$, $R^2$, $R^3$, and $R^4$ each represent an alkyl group having 1 to 4 carbon atoms; $X^1$ and $X^2$ each represent an alkyl group having 1 to 4 carbon atoms, an alkoxy group having 1 to 4 carbon atoms or a halogen atom; Y represents an alkanediyl group having 1 to 4 carbon atoms; and a plurality of $R^1$s, $R^2$s, $R^3$s, $R^4$s, $X^1$s, $X^2$s, and Ys, where present per molecule, may be the same or different.

DETAILED DESCRIPTION OF THE INVENTION

The siloxane compound that can be used in the invention is described first.

The siloxane compound used in the invention has at least one —HSiRO— moiety (wherein R represents a hydrogen atom, a hydrocarbon group having 1 to 8 carbon atoms, an alkoxy group having 1 to 8 carbon atoms, or a phenoxy group) per molecule. The siloxane compound has hydrogen directly bonded to the silicon atom of its siloxane group. This is the very site at which polymerization occurs to cause such disadvantages as solid or gel formation in conventional thin film forming materials containing the siloxane compound as a precursor.

The siloxane compound used in the invention includes a cyclic siloxane compound represented by general formula (I) below and a linear siloxane compound represented by general formula (II) below. The cyclic siloxane compound and the linear siloxane compound are especially useful as a thin film precursor in a CVD or MOD process.

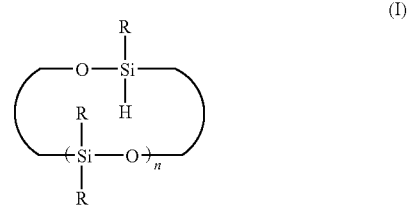

wherein n represents 2 to 7; R represents a hydrogen atom, a hydrocarbon group having 1 to 8 carbon atoms, an alkoxy group having 1 to 8 carbon atoms or a phenoxy group; and a plurality of Rs per molecule may be the same or different.

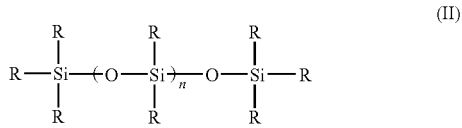

wherein n represents 0 to 5; R represents a hydrogen atom, a hydrocarbon group having 1 to 8 carbon atoms, an alkoxy group having 1 to 8 carbon atoms or a phenoxy group, provided that at least one of Rs is a hydrogen atom; and a plurality of Rs per molecule may be the same or different.

In the siloxane compounds of the invention, the hydrocarbon group having 1 to 8 carbon atoms as represented by R includes an alkyl group, e.g., methyl, ethyl, propyl, isopropyl, butyl, sec-butyl, tert-butyl, isobutyl, amyl, isoamyl, tert-amyl, hexyl, cyclohexyl, cyclohexylmethyl, 2-cyclohexylethyl, heptyl, isoheptyl, tert-heptyl, octyl, isooctyl, tert-octyl or 2-ethylhexyl; an alkenyl group, e.g., vinyl, 1-methylethen-1-yl, propen-1-yl, propen-2-yl, propen-3-yl, buten-1-yl, buten-2-yl, 2-methylpropen-3-yl, 1,1-dimethylethen-2-yl or 1,1-dimethylpropen-3-yl; and an aryl group, e.g., phenyl, 2-methylphenyl, 3-methylphenyl, 4-methylphenyl, 4-vinylphenyl, 2,3-dimethylphenyl, 2,4-dimethylphenyl, 2,5-dimethylphenyl, 2,6-dimethylphenyl, 3,4-dimethylphenyl or 3,5-dimethylphenyl; and an aralkyl group, e.g., benzyl, 2-methylbenzyl, 3-methylbenzyl, 4-methylbenzyl or styryl. The alkoxy group having 1 to 8 carbon atoms as represented by R includes methoxy, ethoxy, propoxy, isopropoxy, butoxy, sec-butoxy, tert-butoxy, isobutoxy, amyloxy, isoamyloxy, tert-amyloxy, hexyloxy, cyclohexyloxy, heptyloxy, isoheptyloxy, tert-heptyloxy, octyloxy, isooctyloxy, tert-octyloxy or 2-ethylhexyloxy.

Specific examples of the cyclic siloxane compound of general formula (I) include 2,4,6-trimethylcyclotrisiloxane, 2,4,6,8-tetramethylcyclotetrasiloxane, 2,4,6,8,10-pentamethylcyclopentasiloxane, 2,4,6,8,10,12-hexamethylcyclohexasiloxane, 2,4,6,8,10,12,14-heptamethylcycloheptasiloxane, 2,4,6,8,10,12,14,16-octamethylcyclooctasiloxane, 2,4,6-triethylcyclotrisiloxane, 2,4,6,8-tetraethylcyclotetrasiloxane, 2,4,6,8,10-pentaethylcyclopentasiloxane, 2,4,6,8,10,12-hexaethylcyclohexasiloxane, 2,4,6-triphenylcyclotrisiloxane, 2,4,6,8-tetraphenylcyclotetrasiloxane, 2,4,6,8,10-pentaphenylcyclopentasiloxane, and 2,4,6,8,10,12-hexaphenylcyclohexasiloxane.

Specific examples of the linear siloxane compound of general formula (II) include 1,3-dimethyldisiloxane, 1,1,3-trimethyldisiloxane, 1,1,3,3-tetramethyldisiloxane, 1,1,1,3,3-pentamethyldisiloxane, 1,3-diethyldisiloxane, 1,1,3,3-tetraethyldisiloxane, 1,1,3-triethyldisiloxane, 1,1,1,3,3-pentaethyldisoloxane, 1,3-diphenyldisiloxane, 1,1,3,3-tetraphenyldisiloxane, 1,1,3-triphenyldisiloxane, 1,3-dimethyl-1,3-diphenyldisiloxane, 1,3-diethyl-1,3-diphenyldisiloxane, 1,1,3,3,5,5,5-heptamethyltrisiloxane, 1,1,1,3,5,5,5-heptamethyltrisiloxane, 1,1,1,5,5,5-hexamethyl-3-ethyltrisiloxane, 1,1,1,5,5,5-hexamethyltrisiloxane, 1,1,3,3,5,5-hexamethyltrisiloxane, 1,1,1,3,3,5-hexamethyltrisiloxane, 1,1,3,5,5-pentamethyltrisiloxane, 1,1,3,3,5-pentamethyltrisiloxane, 1,1,1,3,5-pentamethyltrisiloxane, 1,1,3,3-tetramethyltrisiloxane, 1,1,1,3-tetramethyltrisiloxane, 1,1,3,5-tetramethyltrisiloxane, 1,3,5-trimethyltrisiloxane, 1,1,5,5-tetramethyl-3-phenyltrisiloxane, 3-methyl-1,1,1,5,5,5-hexaphenyltrisiloxane, 1,1,1,3,5,7,7,7-octamethyltetrasiloxane, and 1,1,3,3,5,5,7,7-octamethyltetrasiloxane.

Of the siloxane compounds used in the invention those in which the alkyl group as R is a methyl group are particularly advantageous in that they are capable of forming an SiO-based thin film with a small dielectric constant (low-K thin film). The cyclic siloxane compounds of general formula (I) are also particularly advantageous in that they are capable of forming a thin film with good electrical characteristics. Inter alia, 2,4,6,8-tetramethylcyclotetrasiloxane has a high vapor pressure and provides a thin film with satisfactory characteristics and is therefore suitable when the composition of the invention is used as a material of thin film formation processes involving vaporization of a precursor, such as CVD inclusive of ALD.

The phenol compound that can be used in the invention will then be described. The phenol compound represented by general formulae (1) or (2) functions as a stabilizer against polymerization of the siloxane compound having —HSiRO— (wherein R represents a hydrogen atom, a hydrocarbon group having 1 to 8 carbon atoms, an alkoxy group having 1 to 8 carbon atoms, or a phenoxy group).

In general formulae (1) and (2), the alkyl group having 1 to 4 carbon atoms as represented by $R^1$ to $R^4$ includes methyl, ethyl, propyl, isopropyl, butyl, sec-butyl, and tert-butyl. The alkyl group having 1 to 4 carbon atoms as represented by $X^1$ and $X^2$ includes those enumerated above as examples of $R^1$ to $R^4$. The alkoxy group having 1 to 4 carbon atoms includes methoxy, ethoxy, propoxy, isopropoxy, butoxy, sec-butoxy, and tert-butoxy. The halogen atom includes fluorine, chlorine, bromine, and iodine. The alkanediyl group as represented by Y includes methanediyl, ethane-1,2-diyl, ethane-1,1-diyl, propane-1,3-diyl, propane-1,2-diyl, propane-1,1-diyl, butane-1,4-diyl, butane-1,3-diyl, butane-1,2-diyl, butane-1,1-diyl, 2-methylpropane-1,1-diyl, 2-methylpropane-1,2-diyl, and 2-methylpropane-1,3-diyl.

Specific examples of the phenol compound according to the invention include compound Nos. 1 through 36 shown below. Compound Nos. 1 to 20 are phenol compounds of general formula (1), and compound Nos. 21 to 36 are those of general formula (2).

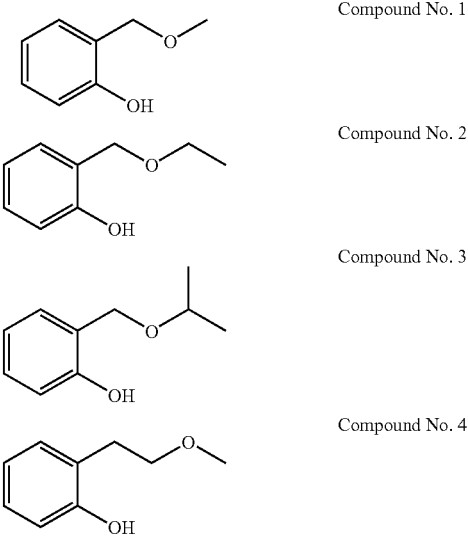

Compound No. 1

Compound No. 2

Compound No. 3

Compound No. 4

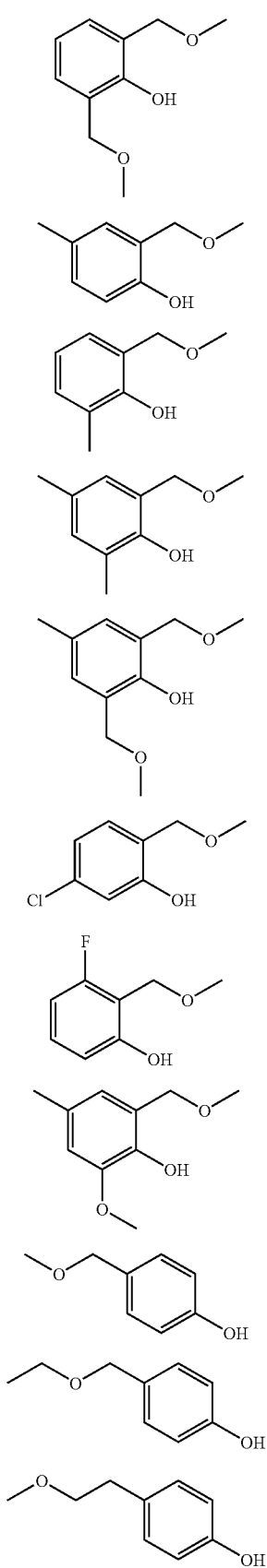
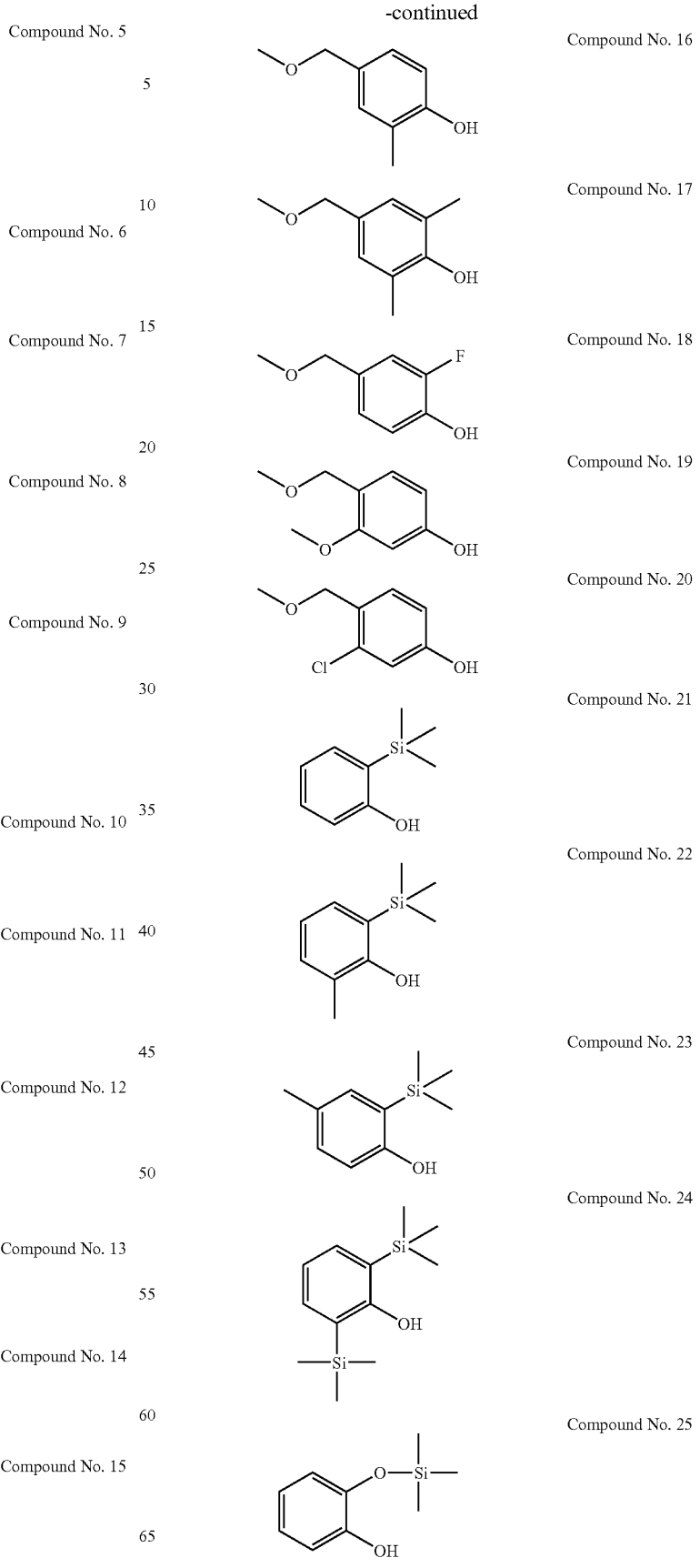

-continued

Compound No. 26 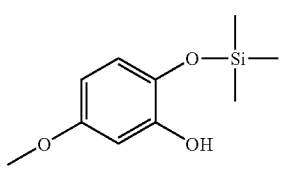

Compound No. 27 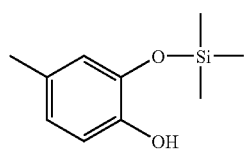

Compound No. 28 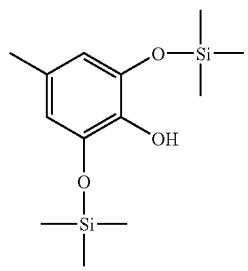

Compound No. 29 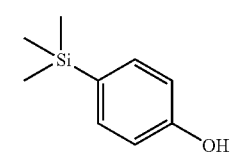

Compound No. 30 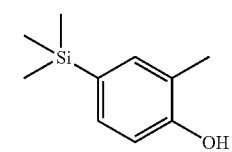

Compound No. 31 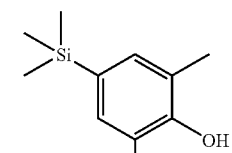

Compound No. 32 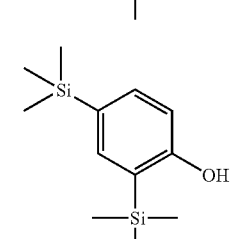

Compound No. 33 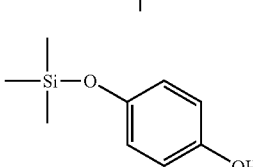

Compound No. 34 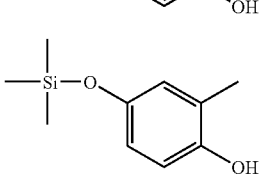

-continued

Compound No. 35 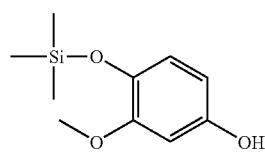

Compound No. 36 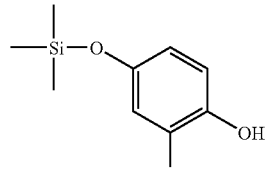

Of the phenol compounds according to the present invention, those having a substituent —Y—O—R' or a substituent —(O)$_m$—SiR$^2$R$^4$—R$^3$ at the ortho position of the phenol nucleus, i.e., compounds represented by general formulae (3) or (4) below are preferred for their excellent stabilizing effect on the siloxane compounds having —HSiRO— (wherein R represents a hydrogen atom, a hydrocarbon group having 1 to 8 carbon atoms, an alkoxy group having 1 to 8 carbon atoms, or a phenoxy group).

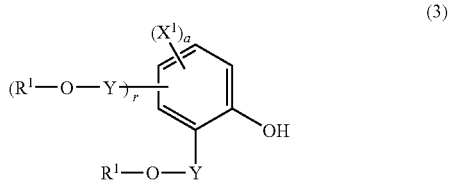 (3)

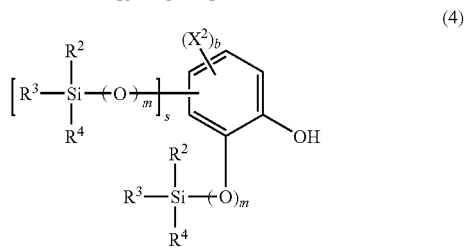 (4)

wherein a and b each represent an integer of 0 to 4; m represents 0 or 1; r and s each represent 0 or 1; R$^1$, R$^2$, R$^3$, and R$^4$ each represent an alkyl group having 1 to 4 carbon atoms; X$^1$ and X$^2$ each represent an alkyl group having 1 to 4 carbon atoms, an alkoxy group having 1 to 4 carbon atoms or a halogen atom; Y represents an alkanediyl group having 1 to 4 carbon atoms; and a plurality of R$^1$s, R$^2$s, R$^3$s, R$^4$s, X$^1$s, X$^2$s, and Ys, where present per molecule, may be the same or different.

The composition according to the invention contains the siloxane compound having at least one —HSiRO— moiety (wherein R represents a hydrogen atom, a hydrocarbon group having 1 to 8 carbon atoms, an alkoxy group having 1 to 8 carbon atoms, or a phenoxy group) per molecule and a stabilizer comprising at least one phenol compound represented by formula (1) or (2). The amount of the phenol compound as a stabilizer is 0.0001 to 1 part by mass, preferably 0.001 to 0.1 parts by mass, still preferably 0.002 to 0.05 parts by mass, per 100 parts by mass of the siloxane compound. When used in an amount less than 0.0001 parts by mass, the phenol compound fails to produce necessary effects of addition. Use of more than 1 part by mass of the phenol compound produces no further increase in effect or can affect the resulting thin film characteristics.

Use of the composition according to the invention will be explained.

The composition of the invention is useful as a material of silicon-containing thin film formation. It is especially useful as a material of silicon-based thin film formation involving a vaporizing step such as chemical vapor deposition (CVD) process inclusive of ALD process. The composition of the invention is also useful as a material of wet process thin film formation as well as CVD.

When the material for thin film formation of the invention is for chemical vapor deposition (CVD), the form of the material is selected as appropriate to the procedures of the CVD process adopted, such as a source delivery system.

The source delivery system includes a vapor delivery system in which the material for CVD is vaporized by heating and/or pressure reduction in a container and introduced into a deposition reaction site, if desired, together with a carrier gas, e.g., argon, nitrogen or helium, and a liquid delivery system in which the material for CVD is delivered in the form of a liquid or a solution to a vaporizer, where it is vaporized by heating and/or pressure reduction and then led to a deposition reaction site. When applied to the vapor delivery system, the composition of the invention per se, which contains the siloxane compound and the phenol compound, is a material for CVD. In the case of the liquid delivery system, the composition of the invention, which contains the siloxane compound and the phenol compound, per se or the composition of the invention in the form of a solution of the siloxane compound and the phenol compound in an organic solvent is a material for CVD.

In a multi-component CVD process for forming a multi-component thin film, the source delivery systems includes a system in which a plurality of the materials are separately vaporized and delivered (hereinafter referred to as a multi-source system) and a system in which a plurality of the materials are previously mixed at a prescribed ratio, and the mixture is vaporized and delivered (hereinafter referred to as a single source system).

The organic solvent that can be used in the composition of the invention is not particularly limited, and any widely known organic solvent is useful. Examples are acetic esters, such as ethyl acetate, butyl acetate, and methoxyethyl acetate; ethers, such as tetrahydrofuran, tetrahydropyran, morpholine, ethylene glycol dimethyl ether, diethylene glycol dimethyl ether, triethylene glycol dimethyl ether, dibutyl ether, and dioxane; ketones, such as methyl butyl ketone, methyl isobutyl ketone, ethyl butyl ketone, dipropyl ketone, diisobutyl ketone, methyl amyl ketone, cyclohexanone, and methylcyclohexanone; hydrocarbons, such as hexane, cyclohexane, methylcyclohexane, dimethylcyclohexane, ethylcyclohexane, heptane, octane, toluene, and xylene; hydrocarbons having a cyano group, such as 1-cyanopropane, 1-cyanobutane, 1-cyanohexane, cyanocyclohexane, cyanobenzene, 1,3-dicyanopropane, 1,4-dicyanobutane, 1,6-dicyanohexane, 1,4-dicyanocyclohexane, and 1,4-dicyanobenzene; pyridine, and lutidine. A solvent or a mixture of solvents to be used is selected according to, for example, solubility of the solute and the boiling temperature or ignition temperature in relation to the working temperature. In using these organic solvents, the total concentration of the siloxane compound component and other precursor(s), if used in combination according to necessity as described infra, in the organic solvent is preferably 0.01 to 2.0 mol/l, still preferably 0.05 to 1.0 mol/l.

Where the composition of the invention is used as a material for multi-component CVD in a multi-source system or a single source system, other precursors that can be used in combination with the siloxane compound of the invention are not particularly limited, and any precursors well-known in the art for use as CVD materials can be used.

The other precursors include volatile compounds of metals or inorganic elements. The element species of the other precursors include group 1 elements, e.g., lithium, sodium, potassium, rubidium, and cesium; group 2 elements, e.g., beryllium, magnesium, calcium, strontium, and barium; group 3 elements, e.g., scandium, yttrium, lanthanoid elements (lanthanum, cerium, praseodymium, neodymium, promethium, samarium, europium, gadolinium, terbium, dysprosium, holmium, erbium, thulium, ytterbium, and lutetium), and actinoid elements; group 4 elements, e.g., titanium, zirconium, and hafnium; group 5 elements, e.g., vanadium, niobium, and tantalum; group 6 elements, e.g., chromium, molybdenum, and tungsten; group 7 elements, e.g., manganese, technetium, and rhenium; group 8 elements, e.g., iron, ruthenium, and osmium; group 9 elements, e.g., cobalt, rhodium, and iridium; group 10 elements, e.g., nickel, palladium, and platinum; group 11 elements, e.g., copper, silver, and gold; group 12 elements, e.g., zinc, cadmium, and mercury; group 13 elements, e.g., boron, aluminum, gallium, indium, and thallium; group 14 elements, e.g., germanium, tin, and lead; group 15 elements, e.g., phosphorus, arsenic, antimony, bismuth, and group 16 elements, e.g., selenium, tellurium, and polonium.

If desired, the composition of the invention can contain a nucleophilic reagent other than the phenol compound to stabilize the siloxane compound of the invention and other precursor. Examples of the nucleophilic reagent include ethylene glycol ethers, such as glyme, diglyme, triglyme, and tetraglyme; crown ethers, such as 18-crown-6, dicyclohexyl-18-crown-6, 24-crown-8, dicyclohexyl-24-crown-8, and dibenzo-24-crown-8; polyamines, such as ethylenediamine, N,N'-tetramethylethylenediamine, diethylenetriamine, triethylenetetramine, tetraethylenepentamine, pentaethylenehexamine, 1,1,4,7,7-pentamethyldiethylenetriamine, 1,1,4,7,10,10-hexamethyl-triethylenetetramine, and triethoxytriethyleneamine; cyclic polyamines, such as cyclam and cyclen; heterocyclic compounds, such as pyridine, pyrrolidine, piperidine, morpholine, N-methylpyrrolidine, N-methylpiperidine, N-methylmorpholine, tetrahydrofuran, tetrahydropyran, 1,4-dioxane, oxazole, thiazole, and oxathiolane; β-keto esters, such as methyl acetoacetate, ethyl acetoacetate, and 2-methoxyethyl acetoacetate; and β-diketones, such as acetylacetone, 2,4-hexanedione, 2,4-heptanedione, 3,5-heptanedione, and dipivaroylmethane. The nucleophilic reagent as a stabilizer is used in an amount of 0.1 to 10 mol, preferably 1 to 4 mol, per mole of the precursor.

The contents, in the composition of the invention, of impurities other than the components constituting the composition, including impurity metal elements, impurity halogens (e.g., impurity chlorine), and impurity organic matter, should be minimized. The impurity metal element content is preferably 100 ppb or less, still preferably 10 ppb or less, for every element, and a total impurity metal content is preferably 1 ppm or less, still preferably 100 ppb or less. The impurity halogen content is preferably 100 ppm or less, still preferably 10 ppm or less, even still preferably 1 ppm or less. The total impurity organic matter content is preferably 500 ppm or less, still preferably 50 ppm or less, even still preferably 10 ppm or less. A water content of the composition causes particle generation in the composition (material for thin film formation) or during CVD. Therefore, it is advisable to minimize the water contents of the precursor, the organic solvent, and the nucleophilic reagent by reducing their water contents on use. The water content of each of the precursor, organic solvent, and nucleophilic reagent is preferably not more than 10 ppm.

In order to reduce or prevent contamination of a thin film with particles, it is desirable for the composition of the invention to have not more than 100 particles greater than 0.3 μm, more desirably not more than 1000 particles greater than 0.2 μm, even more desirably not more than 100 particles greater than 0.2 μm, per ml of the liquid phase as measured with a light scattering particle sensor for detecting particles in a liquid phase.

The composition of the invention as a thin film forming material is especially suited for use in CVD. The thin film formation by CVD using the composition of the invention as a CVD material is not particularly restricted by the method of material delivery, the mode of deposition, the film forming conditions, the film forming equipment, and the like. Any conditions and methods commonly known in the art are made use of.

In thin film formation by CVD using the composition of the invention as a CVD material, a reactive gas may be used if necessary to cause the siloxane compound and other precursor, if used, to decompose and/or react. The reactive gas which can be used if necessary includes oxidizing gases, such as oxygen, ozone, nitrogen dioxide, nitrogen monoxide, water vapor, hydrogen peroxide, formic acid, acetic acid, and acetic anhydride; and reducing gases, such as hydrogen. Reactive gases that can be used to form a nitride film include organic amine compounds, such as monoalkylamines, dialkylamines, trialkylamines, and alkylenediamines; hydrazine; ammonia; and nitrogen.

The method of material delivery includes the above-described vapor delivery system, liquid delivery system, multi-source system, and single source system.

The deposition modes include thermal CVD, in which only heat is used to cause the vaporized material or a mixture of the vaporized material and a reactive gas to react to deposit a film, plasma-enhanced CVD (heat and plasma are used), photo-assisted CVD (heat and light are used), photo plasma-assisted CVD (heat, light, and plasma are used), and ALD (atomic layer deposition), in which a deposition reaction of CVD is divided into elementary reaction steps so as to build up a film stepwise on a molecular level.

The film forming conditions include reaction temperature (the substrate temperature), reaction pressure, and deposition rate. The reaction temperature is preferably 160° C. or higher at which the siloxane compound used in the invention reacts sufficiently, still preferably 250° to 800° C. The reaction pressure is from atmospheric pressure to 100 Pa. The deposition rate can be controlled by the material feed conditions (vaporizing temperature and vaporizing pressure) and the reaction temperature and pressure. Too high a deposition rate tends to result in deteriorated characteristics of the resulting thin film, and too low a deposition rate can result in poor productivity. A preferred deposition rate ranges from 0.5 to 5000 nm/min, still preferably 1 to 1000 nm/min. In the case of ALD, the film thickness is controlled by the number of cycles to reach a desired film thickness.

In the thin film formation process, the deposited thin film may be subjected to annealing in an inert gas atmosphere or an oxidizing or reducing atmosphere to obtain improved electrical characteristics. Where step coverage is required, the process can have the step of reflowing. The reflow is conducted usually at 400° to 1200° C., preferably 500° to 800° C.

Applications of the thin films produced from the thin film forming material comprising the composition of the present invention include copper diffusion barrier insulators in using copper wiring and interlater insulators for highly integrated LSIs. The thickness of a thin film formed of the thin film forming material of the invention, which is decided as appropriate to the use, is preferably 1 to 1000 nm.

The composition of the invention is also useful in applications other than the thin film forming material, such as a resin modifier, a glass modifier, and a ceramic modifier.

EXAMPLES

The present invention will now be illustrated in greater detail with reference to Examples and Comparative Examples, but it should be understood that the invention is not construed as being limited thereto.

Examples 1 to 6 and Comparative Examples 1 to 3

In a 100 ml flask purged with dry argon were put 20 g of 2,4,6,8-tetramethylcyclotetrasiloxane (hereinafter sometimes abbreviated as TMCTS) and 4 mg of the phenol compound shown in Table 1 below. The 2,4,6,8-tetramethylcyclotetrasiloxane used had previously been analyzed with a gas chromatograph (column: 007-1-25W-5.0F from QUADREX) equipped with an FID detector.

The flask containing the 2,4,6,8-tetramethylcyclotetrasiloxane and the phenol compound was maintained at 120° C. and stirred while bubbling with oxygen gas fed at 1.20 l/hr for 24 hours, followed by analyzing with a gas chromatograph (column: 007-1-25W-5.0F from QUADREX) equipped with an FID detector.

The peaks detected by the analyses were assigned to 2,4,6,8-tetramethylcyclotetrasiloxane and a plurality of polymeric compounds resulting from polymerization of 2,4,6,8-tetramethylcyclotetrasiloxane. The sum of the peak area of 2,4,6,8-tetramethylcyclotetrasiloxane and the peak areas of the polymeric compounds being taken as 100, the ratio of the peak area of 2,4,6,8-tetramethylcyclotetrasiloxane is shown in Table 1.

TABLE 1

| | | TMCTS Peak Ratio (%) | | |
|---|---|---|---|---|
| | Phenol Compound | before mixing of phenol compound | after 24 hour heating with stirring | Difference (Increase of Polymeric Compounds) |
| Example 1 | Compound No. 1 | 99.67 | 99.39 | 0.28 |
| Example 2 | Compound No. 4 | 100 | 99.78 | 0.22 |
| Example 3 | Compound No. 9 | 100 | 99.66 | 0.34 |
| Example 4 | Compound No. 15 | 99.40 | 98.94 | 0.46 |
| Example 5 | Compound No. 21 | 99.97 | 99.48 | 0.49 |
| Example 6 | Compound No. 25 | 99.64 | 99.61 | 0.03 |
| Compara. Example 1 | 2,6-Di-t-butyl-4-methylphenol | 99.48 | 98.22 | 1.26 |
| Compara. Example 2 | 4-Methoxyphenol | 99.66 | 98.52 | 1.14 |
| Compara. Example 3 | 2-Methoxyphenol | 99.79 | 99.16 | 0.63 |

It was confirmed from the results in Table 1 that the composition of the present invention containing the specific phenol compound enjoys a high stabilizing effect specific on the siloxane compound against polymerizing. Thus, the composition of the invention is useful as a material of thin film formation.

INDUSTRIAL APPLICABILITY

The composition of the invention is a siloxane compound-containing composition having excellent stability and useful as a material for thin film formation.

What is claimed is:

1. A composition comprising 100 parts by mass of a siloxane compound having —HSiRO— (wherein R represents a hydrogen atom, a hydrocarbon group having 1 to 8 carbon atoms, an alkoxy group having 1 to 8 carbon atoms, or a phenoxy group) and 0.0001 to 1 part by mass of at least one phenol compound represented by general formula (1) or (2) below as a stabilizer

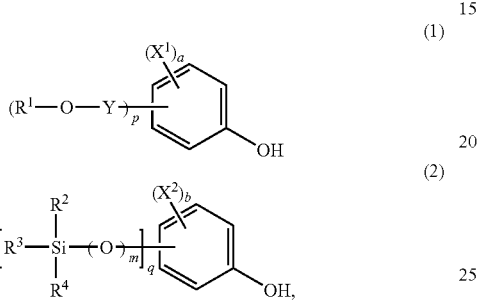

wherein a and b each represent an integer of 0 to 4; m represents 0 or 1; p and q each represent 1 or 2; $R^1$, $R^2$, $R^3$, and $R^4$ each represent an alkyl group having 1 to 4 carbon atoms; $X^1$ and $X^2$ each represent an alkyl group having 1 to 4 carbon atoms, an alkoxy group having 1 to 4 carbon atoms or a halogen atom; Y represents an alkanediyl group having 1 to 4 carbon atoms; and a plurality of $R^1$, $R^2$, $R^3$, $R^4$, $X^1$, $X^2$ or Y, where present per molecule, may be the same or different.

2. A composition comprising 100 parts by mass of a siloxane compound having —HSiRO— (wherein R represents a hydrogen atom, a hydrocarbon group having 1 to 8 carbon atoms, an alkoxy group having 1 to 8 carbon atoms, or a phenoxy group) and 0.0001 to 1 part by mass of at least one phenol compound represented by general formula (3) or (4) below as a stabilizer

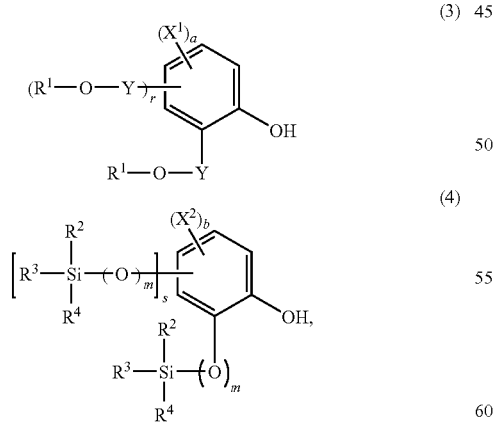

wherein a and b each represent an integer of 0 to 4; m represents 0 or 1; r and s each represent 0 or 1; $R^1$, $R^2$, $R^3$, and $R^4$ each represent an alkyl group having 1 to 4 carbon atoms; $X^1$ and $X^2$ each represent an alkyl group having 1 to 4 carbon atoms, an alkoxy group having 1 to 4 carbon atoms or a halogen atom; Y represents an alkanediyl group having 1 to 4 carbon atoms; and a plurality of $R^1$, $R^2$, $R^3$, $R^4$, $X^1$, $X^2$ or Y, where present per molecule, may be the same or different.

3. The composition according to claim 1, wherein the siloxane compound is a cyclic siloxane compound represented by formula (1):

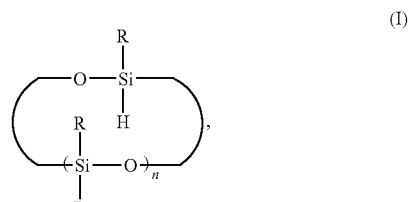

wherein n represents 2 to 7; R represents a hydrogen atom, a hydrocarbon group having 1 to 8 carbon atoms, an alkoxy group having 1 to 8 carbon atoms or a phenoxy group; and a plurality of R per molecule may be the same or different.

4. The composition according to claim 1, wherein the siloxane compound is 2,4,6,8-tetramethylcyclotetrasiloxane.

5. The composition according to claim 1, which is suitable for use as a material for thin film formation by chemical vapor deposition (CVD) process.

6. The composition according to claim 2, wherein the siloxane compound is a cyclic siloxane compound represented by formula (I):

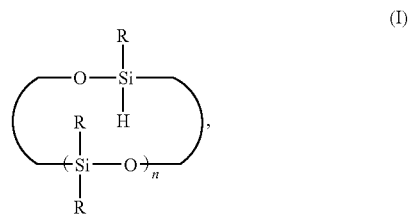

wherein n represents 2 to 7; R represents a hydrogen atom, a hydrocarbon group having 1 to 8 carbon atoms, an alkoxy group having 1 to 8 carbon atoms or a phenoxy group; and a plurality of R per molecule may be the same or different.

7. The composition according to claim 2, wherein the siloxane compound is 2,4,6,8-tetramethylcyclotetrasiloxane.

8. The composition according to claim 5, wherein the thin film formation is by atomic layer deposition (ALP) process or by wet process.

9. A method of forming a thin film, comprising applying the composition according to claim 1 to a substrate.

10. The method according to claim 9, further comprising performing a chemical vapor deposition (CVD) process.

* * * * *